United States Patent [19]

Engelhard et al.

[11] 4,213,849

[45] Jul. 22, 1980

[54] METHOD OF USING CATALYSTS FOR REFORMING OR ISOMERIZING HYDROCARBONS

[75] Inventors: Philippe Engelhard, Le Havre; Michel Legendre, Montivillier; Guy Paris, Le Havre; Georges Szabo, Le Havre, all of France

[73] Assignee: Compagnie Francaise de Raffinage, Paris, France

[21] Appl. No.: 28,444

[22] Filed: Apr. 9, 1979

Related U.S. Application Data

[62] Division of Ser. No. 784,516, Apr. 4, 1977, Pat. No. 4,159,257.

[30] Foreign Application Priority Data

Apr. 5, 1976 [FR] France .................................. 76 09831

[51] Int. Cl.² ........................................... C10G 35/08
[52] U.S. Cl. .................................... 208/139; 585/482; 585/669; 585/671; 585/747
[58] Field of Search ................ 208/139; 585/482, 669, 585/671, 747

[56] References Cited

U.S. PATENT DOCUMENTS

| | | | |
|---|---|---|---|
| 3,389,092 | 6/1968 | Sanford et al. | 252/455 R |
| 3,553,281 | 1/1971 | Gobel et al. | 252/442 |
| 3,657,153 | 4/1972 | Bucur et al. | 252/455 |
| 3,700,588 | 10/1972 | Weisans et al. | 252/442 |
| 3,702,293 | 11/1972 | Hayes et al. | 252/442 |
| 3,707,509 | 12/1972 | Georgescu et al. | 252/442 |
| 3,822,221 | 7/1974 | Weisans et al. | 252/466 PT |
| 3,864,241 | 2/1975 | Rausch | 208/139 |

Primary Examiner—C. Davis
Attorney, Agent, or Firm—A. Thomas S. Safford

[57] ABSTRACT

The improvement of the preferred Pt-Sn on alumina bimetallic catalyst (and similar catalysts) for hydrotreatment of hydrocarbons, comprising the catalyst further containing silicon in combined form.

40 Claims, 1 Drawing Figure

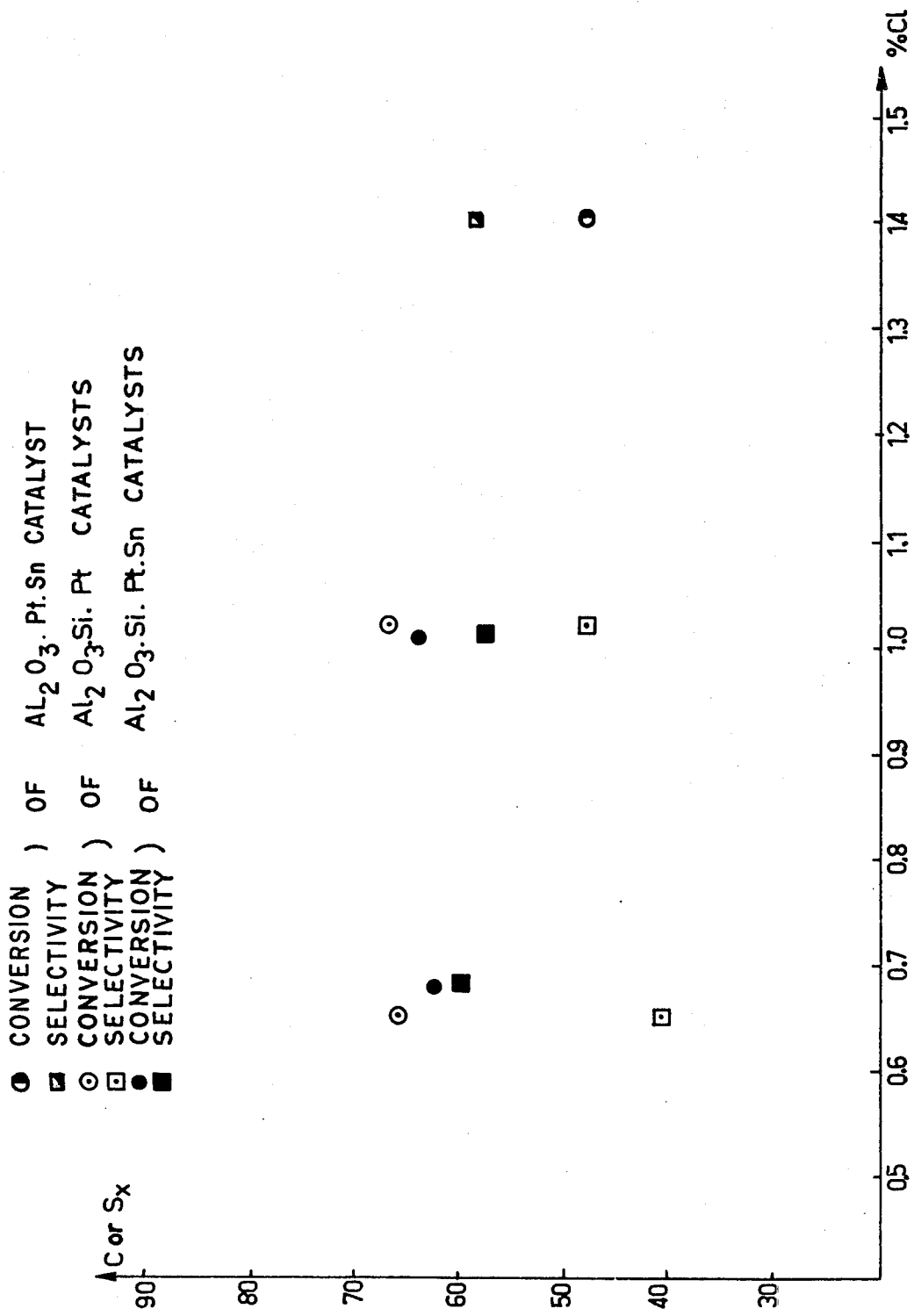

METHOD OF USING CATALYSTS FOR REFORMING OR ISOMERIZING HYDROCARBONS

This is a division of application Ser. No. 784,516, filed Apr. 4, 1977, and now U.S. Pat. No. 4,159,257.

The present invention relates to new catalysts for the hydrotreatment of hydrocarbons, a process for their preparation, and their use in the hydroreforming and isomerization of hydrocarbons.

By catalytic hydrotreating processes are meant treatments applied to hydrocarbon charges in the presence of hydrogen and a catalyst which involve, separately or simultaneously, hydrogenation, dehydrogenation, isomerization, cyclization, dehydrocyclization and aromatization reactions.

One example of a process in which these reactions occur simultaneously is catalytic hydroreforming, a process that is employed particularly in treating petroleum fractions intended for the manufacture of gasolines to increase the octane number of such fractions. This process is widely used on account of the present demand for motor-fuel gasoline. Moreover, the current trend toward reduction of the pollution of the atmosphere caused by automotive vehicles calls for the production of gasolines which may be used directly, without adding tetraethyllead to increase the octane rating.

In catalytic hydroreforming, the processing conditions are selected so as to limit cracking reactions and promote dehydrocyclization, dehydrogenation and isomerization reactions.

Particularly when paraffins and naphthenes, respectively, are present in the feedstocks, the dehydrocyclization and dehydrogenation reactions result in the formation of aromatic hydrocarbons which, apart from being of interest as fuels by reason of their high octane number, are suited for use as raw materials in the petrochemical industry.

Another example of a catalytic hydrotreating process is the process for isomerization of hydrocarbons. This process may be employed particularly with aromatic and saturated or olefinic aliphatic hydrocarbons. It may, for example, be used with aromatic hydrocarbons to increase the production of paraxylene, which is of particular interest as a raw material in the manufacture of polyesters.

The most widely used hydrotreating catalysts are those which contain a platinum-group metal, usually platinum, supported on a refractory oxide mineral of large specific surface, such as alumina, for example. Since the price of platinum is very high, the tendency is to use bi- or trimetallic catalysts, which permit the amount of platinum deposited on the carrier to be reduced and aging of the catalyst to be retarded.

Thus, French Pat. No. 2,006,803, for example, describes a catalyst comprising alumina, at least one platinum-group metal, and rhenium.

French Pat. No. 2,030,338 describes a catalyst containing iridium and a metal selected from the group consisting of gold, silver and copper.

French Pat. No. 2,164,984 describes in particular a catalyst containing platinum, iridium and titanium or zirconium.

Catalysts containing tin and platinum have also been used. U.S. Pat. Nos. 3,700,588 and 3,822,221 owned by the applicants' assignee, describe catalysts containing at least one platinum-group element, for example, platinum and possibly iridium, and at least one element from the group consisting of lead and tin.

U.S. Pat. No. 3,657,153 describes a hydro-reforming catalyst containing alumina, platinum and from 0.05 to 5% of silica.

The applicants have discovered that good results may be obtained using catalysts which contain silicon in addition to a platinum-group metal and tin. The applicants have observed that such catalysts possess improved stability.

An object of the present invention thus is to obtain highly stable hydrotreating catalysts which result in effluents having a very good octane number, give a better liquid-hydrocarbon yield, and have good isomerizing properties.

A first preferred embodiment of the present invention is a hydrocarbon-treating catalyst comprising
(a) a carrier formed essentially of alumina;
(b) a halogen element present in combined form;
(c) from 0.02 to 2%, and preferably from 0.10 to 0.70%, based on the total weight of the catalyst, of at least one platinum-group metal, in free or combined form; and
(d) from 0.02 to 2%, and preferably from 0.05 to 0.60%, based on the total catalyst weight, of tin, in free or combined form; said catalysts being characterized in that they contain from 0.01 to 5%, and preferably from 0.1 to 2%, based on the total catalyst weight, of silicon in combined form.

Under this definition of the invention and throughout this application, the term "platinum-group metal" means one of the following metals: Ruthenium, rhodium, palladium, osmium, iridium and platinum.

The invention relates more particularly to catalysts as defined above in which:
(a) the alumina has a specific surface greater than 15 $m^2$ per gram and a specific pore volume greater than 0.1 cc per gram, and
(b) the halogen content, determined in the elemental form and based on the total catalyst weight, is comprised between 0.1 and 3%, and preferably between 0.6 and 2%.

A second preferred embodiment of the present invention is a process for preparation of catalysts in accordance with the invention, said process comprising:
optional adsorption of an organic compound on the alumina;
contacting the alumina with a silicon compound of the general formula

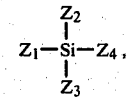

where $Z_1$, $Z_2$, $Z_3$ and $Z_4$ may be a halogen atom or a hydrocarbon radical having from one to four carbon atoms, said contacting with the silicon compound being possibly followed by hydrolysis, the latter being followed by calcination at a temperature comprised between 300° and 700° C., and preferably between 500° and 600° C.;

at least one impregnation of the alumina with at least one solution containing at least one element selected from the group consisting of the platinum-group metals and tin, said alumina being calcined, after deposition of the platinum-group metals, at a temperature of less than 600° C. and, in the case of platinum, of less than 550° C., and/or subjected to a water wash, and, after deposition of the tin when the latter is deposited first, calcined at a temperature comprised between 400° and 700° C., and preferably at a temperature of less than 600° C., and/or subjected to a water wash; and after the deposition of all metals, at least one calcination at a temperature of less than 550° C.

A third preferred embodiment of the present invention is the use of the catalysts defined above in the hydroreforming of a petroleum fraction which contains less than 10 ppm, and preferably less than 1 ppm, of sulfur and whose boiling temperature at atmospheric pressure is comprised between 35° and 250° C.

A fourth preferred embodiment of the present invention is the use of the catalysts in accordance with the invention in the isomerization of hydrocarbons in the presence of hydrogen.

The most advantageous catalysts are those whose platinum-group metal content is comprised between 0.02 and 2%, based on the total catalyst weight. To obtain satisfactory catalytic properties, the content of said metal is preferably greater than 0.10%; however, for reasons of catalyst cost, it is preferably limited to 0.70%.

The tin content is comprised between 0.02 and 2%, based on the total catalyst weight, since below 0.02% and above 2% the improvement in catalytic properties over a catalyst containing only platinum is negligible. The applicants have further observed that the most efficacious contents are those comprised between 0.02 and 0.60%.

The applicants have found that the most worthwhile silicon contents are those comprised between 0.01 and 5%, and preferably between 0.1 and 2%, based on the total catalyst weight.

The halogen content may be comprised between 0.1 and 3%, and preferably between 0.6 and 2%, based on the total catalyst weight. The halogen present in the catalysts in accordance with the invention is preferably chlorine. It may be introduced into the catalyst composition in a manner known in the art, for example, during the preparation of the carrier and/or during the deposition of the metallic elements; for example, by the use of solutions of metal chlorides.

The catalysts in accordance with the invention may be prepared by known processes of deposition of the silicon, the platinum-group metals, and the tin on the alumina.

The operating procedure which may be employed in the deposition of the silicon for the purpose of preparing the catalysts in accordance with the invention is described particularly in U.S. Pat. No. 3,389,092 and in the article which appeared in IZVESTIYA AKADEMII NAUK SSSR SERIYA KHIMICHESKAYA, volume 5 (1967), pages 1036 to 1044.

The deposition of the silicon, effected preferably before the deposition of the platinum-group metals and of the tin, may be carried out by contacting the alumina with a silicon compound of the general formula

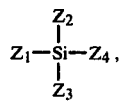

where $Z_1$, $Z_2$, $Z_3$ and $Z_4$ may be a halogen or a hydrocarbon radical having from one to four carbon atoms.

The silicon compound may be silicon tetrachloride, methyltrichlorosilane, dimethyldichlorosilane or trimethylchlorosilane, for example.

Before being contacted with the silicon compound, the alumina is preferably calcined at a temperature comprised between 300° and 700° C., and preferably between 500° and 650° C.

When the silicon compound and the alumina are being contacted with each other, the silicon compound may be in the vapor phase or in solution in a solvent.

Contacting of the silicon compound in the vapor phase may be effected at a pressure below or above atmospheric pressure. The silicon compound in the vapor phase may be pure or diluted in an inert gas such as nitrogen.

Contacting of the silicon compound and the alumina may also be carried out in the liquid phase, the silicon compound being diluted in a solvent such as a paraffinic hydrocarbon or a petroleum fraction.

Before the silicon compound and the alumina are contacted with each other, and after the latter has been calcined at a temperature comprised between 300° and 700° C., and preferably between 500° and 650° C., a certain quantity of an organic compound such as a halogenated hydrocarbon, for example, carbon tetrachloride, dichloropropane or chloroform, may be adsorbed on the alumina to permit better control of the amount of silicon deposited on the carrier. Such adsorption may be carried out in the vapor phase, at a pressure below or above atmospheric pressure. After elimination of the excess of organic compound which has not been adsorbed, for example by placing the alumina under vacuum, the deposition of the silicon may be effected as indicated above.

After the alumina has been contacted with the silicon compound, the latter may possibly be subjected to hydrolysis, for example, by exposing the solid obtained to the ambient atmosphere, the water vapor contained in the air then hydrolyzing the silicon compound.

After contacting the alumina with the silicon compound, and after hydrolysis if the process of preparation includes that step, the alumina is made to undergo calcination at a temperature comprised between 300° and 700° C., and preferably between 500° and 600° C.

The deposition of the platinum-group metals and of the tin may be carried out by conventional procedures for impregnation of the carrier by means of solutions containing the element or elements to be deposited.

The impregnation of the carrier may be effected:

(a) either with a single solution containing the element or elements to be deposited (b) or with several solutions containing the elements to be deposited.

The platinum may be deposited from a solution of hexachloroplatinic acid, for example.

The deposition of the tin, which preferably takes place before the deposition of the platinum-group metal, may be effected, for example, from solutions of stannous chloride, stannic chloride or any other soluble salt of tin.

When the metals are not deposited simultaneously, the solid obtained may be calcined between depositions at a temperature which in the case of tin is comprised between 400° and 700° C. and is preferably 600° C. or less, said calcination temperature being, in the case of the platinum-group metals, under 600° C. and, in the case of platinum, under 550° C.

In place of or in addition to calcination, the solid obtained may be subjected, between or after the depositions, to a wash with liquid water at a temperature that is preferably less then 100° C.

When all the metals to be deposited have been deposited, the solid obtained is calcined at a temperature of less than 550° C. Before this calcination, and after the last deposition, the solid obtained may, if desired, be made to undergo a water wash for adjustment of the halogen content of said solid.

The acidity of the carrier may be altered by an acid treatment with hydrochloric acid, for example, before the deposition of the elements, during the deposition or between depositions when the latter are not simultaneous.

The catalysts in accordance with the invention may be employed in the hydrotreatment of hydrocarbon charges.

They are particularly well suited for use in processes for the hydroreforming of petroleum fractions intended for the manufacture of high-octane gasolines as well as in processes for the isomerization of aromatic hydrocarbons.

The catalyst may be activated during the hydro-treatment by the addition to the charge of a soluble halogen compound (such as a chloride, for example). It may also be advantageous to presulfurize the catalyst with a sulfurized hydrogen stream, for example, so as to limit the cracking reactions which tend to occur at the start of the treatment.

The hydroreforming operation is carried out under the following conditions:

Temperature: Between 450° and 550° C.
Pressure: Between 5 and 50 bars.
Molar ratio of hydrogen to hydrocarbons: Between 2 and 10.
Space velocity (volume of gas passing over a unit volume of catalyst per hour): Between 0.5 and 5.

The operation of isomerization of aromatic hydrocarbons is carried out under the following conditions:

Temperature: Between 300° and 550° C.
Pressure: Between 5 and 50 bars.
Molar ratio of hydrogen to hydrocarbons: Between 2 and 20.
Space velocity (as defined above) of the charge: Between 0.5 and 5.

As will be shown in the examples which follow, which are in no wise limitative, the applicants have obtained highly satisfactory results with the catalysts in accordance with the invention.

Example 1 relates to the preparation of catalysts in accordance with the invention and of control catalysts.

Example 2 relates to the use of catalysts in accordance with the invention and of control catalysts in the hydroreforming of a charge of normal heptane.

The nature of said charge does not constitute a limitation of the field of use of said catalysts since such a charge is generally used to test the performance of hydroreforming catalysts. The results obtained may therefore be extended to the case where the charge is a fraction intended for the manufacture of high-octane gasoline whose boiling temperature is comprised between 35° and 250° C. and whose sulfur content is less than 10 ppm, and preferably less than 1 ppm.

Example 3 relates to the use of catalysts in accordance with the invention and of control catalysts in the isomerization of a charge consisting of ethylbenzene. This example 3, is illustrated by the single figure, which will be explained in conjunction with the description of example 3.

EXAMPLE 1

This example relates to the preparation from a starting alumina (1) of control catalysts T1 and T2 consisting of platinum, tin, and alumina;

(2) of silicon-containing aluminas A and B which differ with respect to their mode of preparation. In the case of B, dichloropropane has been adsorbed on the alumina prior to contacting with the silicon compound, which has not been done in the case of A;

(3) of control catalysts T3, T4 and T5 prepared from silicon-containing aluminas A and B and incorporating only platinum; and (4) of catalysts D1, D2, D3 and D4 in accordance with the invention.

The starting alumina used consists of extrudates having the following characteristics:

| | |
|---|---|
| Average diameter of extrudates: | 1.5 mm |
| Specific surface: | 190 m$^2$/g |
| Pore volume: | 0.51 cc/g |
| Chlorine content (measured by x-ray fluorescence): | 0.5% by weight of the alumina |

PREPARATION OF CONTROL CATALYSTS T1 and T2

100 g of starting alumina is immersed in 250 cc of and aqueous solution containing 7 cc of hydrochloric acid R.P. and 7 cc of nitric acid R.P. which is circulated for ½ hr.

A second solution containing 0.380 g of stannous chloride, SnCl$_2$·2H$_2$O, 10 cc of hydrochloric acid R.P., and 10 cc of water is then added to the first solution. The resulting solution is circulated for 2 hr.

After draining, the solid obtained is immersed in 80 cc of water which is circulated for 2 hr.

After draining, the solid obtained is immersed in 120 cc of a solution of hexachloroplatinic acid containing 3 g/l of platinum. This solution is circulated for 4 hr.

After draining, the alumina is dried for 1 hr. at 120° C., then calcined at 530° C. for 2 hr.

The composition of the catalysts obtained is given in Table 1 which follows.

Table 1

| Catalyst | Composition of catalyst in wt. % | | |
|---|---|---|---|
| | Platinum | Tin | Chlorine |
| T1 | 0.35 | 0.20 | 0.86 |
| T2 | 0.35 | 0.20 | 1.40 |

PREPARATION OF SILICON-CONTAINING ALUMINA A

The starting alumina is placed in a chamber which may be placed under vacuum. (10$^{-3}$ torr) This chamber is brought to 600° C. for 2 hr. It is then brought to 520° C. under vacuum for 16 hr. Then it is brought back to ambient temperature while being maintained under vacuum.

The chamber is then placed in communication with a balloon flask containing dichlorodimethylsilane at ambient temperature for ½ hr., the pressure of the dichlorodimethylsilane being 70 mm Hg. The chamber is then placed under vacuum for ½ hr.

Then the alumina is exposed to air for 16 hr. at ambient temperature.

The alumina is then calcined in air for 2 hr. at 600° C.

The silicon-containing alumina obtained contains 1% by weight of silicon and 0.7% by weight of chlorine.

PREPARATION OF SILICON-CONTAINING ALUMINA B

The starting alumina is placed in a chamber which may be placed under vacuum. This chamber is brought to 600° C. for 2 hr. It is then brought to 520° C. under vacuum for 16 hr. Then it is brought back to ambient temperature while being maintained under vacuum.

The chamber is then placed in communication with a balloon flask containing dichloropropane at ambient temperature for 1 hr., the pressure of the dichloropropane being 10 mm Hg. The chamber is then placed under vacuum for ½ hr.

Then the chamber is placed in communication with a balloon flask containing dichlorodimethylsilane at ambient temperature for ½ hr., the pressure of the dichlorodimethylsilane being 70 mm Hg. The chamber is then placed under vacuum for ½ hr.

The alumina is then exposed to air for 16 hr. at ambient temperature.

Finally the alumina is calcined in air for 2 hr. at 600° C.

The silicon-containing alumina contains 0.5% by weight of silicon and 1% by weight of chlorine.

PREPARATION OF CONTROL CATALYSTS T3, T4 AND T5

100 g of silicon-containing alumina A or B is immersed in 250 cc of a tenth-normal solution of hydrochloric acid which is circulated for 2 hr.

After draining, the alumina is immersed in 250 cc of a solution of hexachloroplatinic acid containing 1.4 g of platinum per liter. This solution is circulated for 16 hr.

After draining, the alumina is dried at 120° C. for 16 hr., then calcined at 530° C. for 2 hr.

The compositions of the catalysts obtained are given in Table 2 which follows.

Table 2

| Catalyst | Silicon-containing alumina | Composition of catalyst in wt. % | | |
|---|---|---|---|---|
| | | Silicon | Platinum | Chlorine |
| T3 | A | 1.05 | 0.41 | 0.65 |
| T4 | B | 0.67 | 0.37 | 0.91 |
| T5 | B | 0.14 | 0.39 | 1.02 |

PREPARATION OF CATALYSTS D1, D2, D3 and D4

100 g of silicon-containing alumina B is immersed in 250 cc of an aqueous solution containing 7 cc of hydrochloric acid R.P. and 7 cc of nitric acid R.P., which is circulated for ½ hr.

A second solution containing 0.380 of stannous chloride, $SnCl_2 \cdot 2H_2O$, 10 cc of hydrochloric acid R.P., and 10 cc of water is then added to the first solution. The resulting solution is circulated for 2 hr.

After draining, the solid obtained is immersed in 80 cc of water, which is circulated for 2 hr.

After draining, the solid obtained is immersed in 120 cc of a solution of hexachloroplatinic acid containing 3 g/l of platinum. This solution is circulated for 4 hr.

After draining, the alumina is dried for 1 hr. at 120° C., then calcined at 530° C. for 2 hr.

The compositions of the catalysts obtained are given in Table 3 which follows.

Table 3

| Catalyst | Silicon-containing alumina | Composition of catalyst in wt. % | | | |
|---|---|---|---|---|---|
| | | Silicon | Platinum | Tin | Chlorine |
| D1 | B | 0.69 | 0.36 | 0.18 | 0.90 |
| D2 | B | 0.72 | 0.38 | 0.20 | 0.68 |
| D3 | B | 0.50 | 0.34 | 0.20 | 1.01 |
| D4 | B | 0.49 | 0.42 | 0.22 | 0.94 |

EXAMPLE 2

In this example, the control catalysts T1 and T4 and the catalysts D1 and D4 in accordance with the invention are made to undergo a catalytic test under hydrogen pressure relating to the hydroreforming of a charge of normal heptane.

25 cc of catalyst is placed in a reactor. A stream of pure, dry hydrogen is then passed over the catalyst for 2 hr., the temperature of the catalyst being maintained at about 500° C. and the pressure in the reactor being maintained at 7 bars. The charge consisting of normal heptane is then introduced at a space velocity of 2 and at a ratio of moles of hydrogen introduced to moles of normal heptane introduced of 5.

Samples taken from the reactor effluent permit determination of the equivalent octane number of the liquid by applying to the chromatographic analysis of said liquid the ASTM blend numbers in graphs with which a person skilled in the art is familiar.

The tests are run at a fixed octane number, that is to say, as soon as a decrease in octane number is observed, the reactor temperature is raised in order to bring the octane number to the level originally selected, which in this example is 103.

The variation of the reactor temperature as a function of time closely resembles a straight line whose gradient is measured. The less the gradient of the straight line, the more stable the catalyst, since the temperature then needs to be adjusted only very slightly in the course of time to secure the desired octane number. The time required to reach the limit temperature of use of the catalyst then is extended, which is a decided advantage in industrial applications.

The results of the catalytic tests under pressure performed on the catalysts T1, T4, D1 and D4 are presented in Table 4 which follows.

Table 4

| Catalyst | Initial temperature °C. | Temperature gradient as a function of time |
|---|---|---|
| T4 | 496.8 | 0.101 |
| T1 | 514 | 0.073 |
| D1 | 505.7 | 0.031 |
| D4 | 508.8 | 0.065 |

It is apparent from this table that, for a constant octane number, the gradient of the straight line is less steep in the case of catalysts D1 and D4 in accordance with the invention than in the case of the control catalysts T1 and T4, which translates into less rapid degradation of the catalyst and therefore means greater stability. The catalysts in accordance with the invention thus possess greater stability.

EXAMPLE 3

In this example, the control catalysts T2, T3 and T5 and the catalysts D2 and D3 are subjected to catalytic tests relating to the isomerization of ethylbenzene. 20 cc of catalyst is placed in a stainless-steel reactor and a stream of pure, dry hydrogen is passed over the catalyst for 2 hr., the temperature of the catalyst being maintained at about 500° C. and the pressure in the reactor being equal to atmospheric pressure. The charge consisting of ethylbenzene is then introduced at a space velocity of 2 and a ratio of moles of hydrogen introduced to moles of ethylbenzene introduced of 5. The temperature is maintained at about 450° C., the pressure being 30 bars.

The effluents are sampled in the liquid state after 2, 4 and 6 hr., respectively, of operation.

These effluents are analyzed by chromatography.

The catalytic activity is characterized by:

the conversion C of the ethylbenzene, which is the ratio:

$$C = \left\{ \frac{\text{weight of ethylbenzene introduced} - \text{weight of ethylbenzene recovered}}{\text{weight of ethylbenzene introduced}} \right\} \times 100$$

the selectivity $S_x$ for xylenes, which is the ratio:

$$S_x = \left\{ \frac{\text{wt. \% of xylenes formed in effluent}}{\text{wt. \% of ethylbenzene converted}} \right\} \times 100$$

and the selectivity $S_{x+int}$ for xylenes plus intermediates, which is the ratio:

$$S_{x+int} = \frac{\text{wt. \% of (xylenes + intermediates) formed in effluent}}{\text{wt. \% of ethylbenzene converted}} \times 100$$

where the intermediates which are the precursors of xylenes are the naphthenic hydrocarbons having eight carbon atoms, such as ethylcyclohexane, dimethylcyclohexane and the alkylcyclopentanes, as well as paraffinic hydrocarbons having eight carbon atoms.

The results of the tests are present in Table 5 which follows.

Table 5

| Catalyst | Operating time, hr. | C | $S_x$ | $S_{x+int}$ |
|---|---|---|---|---|
| T2 | 2 | 44.8 | 58.8 | 85.4 |
|  | 4 | 47.5 | 58.05 | 82.2 |
|  | 6 | 47.3 | 58.3 | 82.7 |
| T3 | 2 | 73.6 | 37.3 | 70.3 |
|  | 4 | 70.1 | 40.6 | 73.0 |
|  | 6 | 66.3 | 40.8 | 76.8 |
| T5 | 2 | 69.8 | 37.0 | 73.9 |
|  | 4 | 70.8 | 40.8 | 76.0 |
|  | 6 | 67.0 | 47.8 | 79.6 |
| D2 | 2 | 62.7 | 60.8 | 85.2 |
|  | 4 | 62.2 | 65.8 | 90.4 |
|  | 6 | 62.5 | 59.8 | 84.0 |

Table 5-continued

| Catalyst | Operating time, hr. | C | $S_x$ | $S_{x+int}$ |
|---|---|---|---|---|
| D3 | 2 | 70.4 | 61.7 | 84.4 |
|  | 4 | 67.6 | 59.9 | 85.2 |
|  | 6 | 63.6 | 57.7 | 88.7 |

In the accompanying drawing, the activity and the selectivity for xylenes of various catalysts after six hours of operation are plotted as a function of chlorine content.

It will be seen that for the catalysts in accordance with the invention and the control catalysts containing silicon but no tin the conversions are similar but the selectivity is clearly better in the case of the catalysts containing tin, the chlorine contents, moreover, being comparable.

As may also be seen, by comparison with the catalysts in accordance with the invention a catalyst containing tin but no silicon gives very poor conversion even with a higher chlorine content, which is regarded as improving conversion.

We claim:

1. Method for the reforming of hydrocarbon fractions whose sulfur content is under 10 ppm, and whose boiling temperature under atmospheric pressure is between 35° and 250° C., comprising the use of a catalyst, in the presence of hydrogen, wherein said carrier is formed essentially of alumina, having between 0.1 and 3% of halogen present in a form combined with at least one other catalyst component, and further comprising on said carrier:
   (a) from 0.02 to 2% of at least one platinum-group metal ingredient,
   (b) from 0.02 to 2% of a tin ingredient,
   (c) from 0.01 to 5% of a silicon ingredient, said percentages being based on the total catalyst weight per elemental form of each ingredient, said catalyst having been prepared by a process comprising the following steps:
   calcining said alumina at between 300° and 700° C., contacting said alumina with a silicon compound of the general formula:

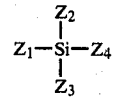

where $Z_1$, $Z_2$, $Z_3$, and $Z_4$ are each a halogen atom or a hydrocarbon radical having from one to four carbon atoms, said contacting step being followed by calcination at between 300° and 700° C.;

at least one impregnation of the alumina with at least one solution containing a compound of at least one element from the group consisting of the platinum-group metals and tin; said alumina being calcined after deposition of the platinum-group metals, at a temperature of less than 600° C. and, in the case of platinum at less than 550° C., and/or subjected to a water wash, and, after deposition of the tin when tin is deposited first, calcined at between 400° and 700° C. and/or subjected to a water wash; and after the deposition of all metals, at least one calcination at a temperature of less than 550° C., incorporating said halogen on said carrier during preparation of the carrier or deposition of said ingredients or both.

2. Process in accordance with claim 1, wherein alumina has a specific surface greater than 15 m² per gram and a specific pore volume greater than 0.1 cc per gram.

3. Process in accordance with claim 1, wherein the catalyst's content is between 0.6 and 2% based on the total catalyst weight.

4. A process in accordance with claim 1, having been prepared by a process further comprising adsorbing a halogenated hydrocarbon on said alumina prior to said contacting step in an amount effective to control the amount of silicon deposited on the carrier by said contacting step.

5. Process in accordance with claim 4, wherein the catalyst's halogen content is between 0.6 and 2%, based on the total catalyst weight.

6. A process in accordance with claim 4, wherein said halogenated hydrocarbon is carbon tetrachloride, dichloropropane or chloroform.

7. A process according to claim 1, wherein the range of said platinum-group metals are from 0.10 to 0.70%, of said tin is from 0.05 to 0.60%, and of said silicon is from 0.1 to 2%.

8. Process in accordance with claim 7, wherein the catalyst's halogen content is between 0.6 and 2%, based on the total catalyst weight.

9. Process in accordance with claim 1, wherein the platinum-group metal is platinum.

10. Process in accordance with claim 5, wherein the platinum-group metal is platinum.

11. Process in accordance with claim 1, wherein the halogen contained in the catalyst is chlorine.

12. Process in accordance with claim 9, wherein the halogen contained in the catalyst is chlorine.

13. Process in accordance with claim 10, wherein the halogen contained in the catalyst is chlorine.

14. A process in accordance with claim 1, further comprising adsorbing a halogenated hydrocarbon on the alumina prior to said contacting step in an amount effective to control the amount of silicon deposited on the carrier by said contacting step.

15. A process in accordance with claim 1, further comprising such contacting with a silicon compound being followed first by hydrolysis.

16. A process in accordance with claim 14, further comprising such contacting with a silicon compound being followed first by hydrolysis.

17. A process in accordance with claim 1, wherein the calcining after the contacting with a silicon compound is between 500° and 600° C. and after the deposition of tin first is under 600° C.

18. A process in accordance with claim 14, further comprising calcining said alumina at between 300° and 700° C. before said adsorption step.

19. Process in accordance with claim 1 the silicon compound is selected from the group consisting of dimethyldichlorosilane, silicon tetrachloride, trimethylchlorosilane and methyltrichlorosilane.

20. Process in accordance with claim 1 the silicon compound is selected from the group consisting of dimethyldichlorosilane, silicon tetrachloride, trimethylchlorosilane and methyltrichlorosilane.

21. Method for the isomerization hydrocarbons in the presence of hydrogen, comprising the use of a catalyst wherein said carrier is formed essentially of alumina, having between 0.1 and 3% of halogen present in a form combined with at least one other catalyst component, and further comprising on said carrier:

(a) from 0.02 to 2% of at least one platinum-group metal ingredient, (b) from 0.02 to 2% of a tin ingredient, (c) from 0.01 to 5% of a silicon ingredient, said percentages being based on the total catalyst weight per elemental form of each ingredient, said catalyst having been prepared by a process comprising the followings steps:

calcining said alumina at between 300° and 700° C., contacting said alumina with a silicon compound of the general formula:

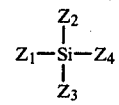

where $Z_1$, $Z_2$, $Z_3$, and $Z_4$ are each a halogen atom or a hydrocarbon radical having from one to four carbon atoms, said contacting step being followed by calcination at between 300° and 700° C.;

at least one impregnation of the alumina with at least one solution containing a compound of at least one element from the group consisting of the platinum-group metals and tin; said alumina being calcined after deposition of the platinum-group metals, at a temperature of less than 600° C. and, in the case of platinum at less than 550° C., and/or subjected to a water wash, and, after deposition of the tin when tin is deposited first, calcined at between 400° and 700° C. and/or subjected to a water wash; and after the deposition of all metals, at least one calcination at a temperature of less than 500° C., incorporating said halogen on said carrier during preparation of the carrier or deposition of said ingredients or both.

22. Process in accordance with claim 21, wherein alumina has a specific surface greater than 15 m² per gram and a specific pore volume greater than 0.1 cc per gram.

23. Process in accordance with claim 21, wherein the catalyst's halogen content is between 0.6 and 2% based on the total catalyst weight.

24. A process in accordance with claim 21, having been prepared by a process further comprising adsorbing a halogenated hydrocarbon on said alumina prior to said contacting step in an amount effective to control the amount of silicon deposited on the carrier by said contacting step.

25. A process in accordance with claim 24, wherein said halogenated hydrocarbon is carbon tetrachloride, dichloropropane or chloroform.

26. A process according to claim 21, wherein the range of said platinum-group metals are from 0.10 to 0.70%, of said tin is from 0.05 to 0.60%, and of said silicon is from 0.1 to 2%.

27. Process in accordance with claim 26, wherein the catalyst's halogen contact is between 0.6 and 2% based on the total catalyst weight.

28. A process in accordance with claim 24, wherein its halogen content is between 0.6 and 2%, based on the total catalyst weight.

29. A process in accordance with claim 21, wherein the platinum-group metal is platinum.

30. A process in accordance with claim 28, wherein the platinum-group metal is platinum.

31. A process in accordance with claim 21, wherein the halogen contained in the catalyst is chlorine.

32. A process in accordance with claim 29, wherein the halogen contained in the catalyst is chlorine.

33. A process in accordance with claim 30, wherein the halogen contained in the catalyst is chlorine.

34. A process in accordance with claim 21, further comprising adsorbing a halogenated hydrocarbon on the alumina prior to said contacting step in an amount effective to control the amount of silicon deposited on the carrier by said contacting step.

35. A process in accordance with claim 21, further comprising said contacting with a silicon compound being followed first by hydrolysis.

36. A process in accordance with claim 34, further comprising such contacting with a silicon compound being followed first by hydrolysis.

37. A process in accordance with claim 21, wherein the calcining after the contacting with a silicon compound is between 500° and 600° C. and after the deposition of tin first is under 600° C.

38. A process in accordance with claim 34, further comprising calcining said alumina at between 300° and 700° C. before said adsorption step.

39. Process in accordance with claim 21 the silicon compound is selected from the group consisting of dimethyldichlorosilane, silicon tetrachloride, trimethylchlorosilane and methyltrichlorosilane.

40. Process in accordance with claim 34 the silicon compound is selected from the group consisting of dimethyldichlorosilane, silicon tetrachloride, trimethylchlorosilane and methyltrichlorosilane.

* * * * *

UNITED STATES PATENT AND TRADEMARK OFFICE
CERTIFICATE OF CORRECTION

PATENT NO. : 4,213,849

DATED : July 22, 1980

INVENTOR(S) : Philippe Engelhard, Michel Legendre, and Georges Szabo

It is certified that error appears in the above-identified patent and that said Letters Patent are hereby corrected as shown below:

Claim 3, line 2, after "catalyst's" insert -halogen--

Claim 20, line 1, replace "1" by --14--.

Signed and Sealed this

Twenty-sixth Day of May 1981

[SEAL]

Attest:

RENE D. TEGTMEYER

Attesting Officer

Acting Commissioner of Patents and Trademarks